(12) United States Patent
Nabatova-Gabain et al.

(10) Patent No.: US 7,280,210 B2
(45) Date of Patent: Oct. 9, 2007

(54) MEASURING METHOD, ANALYZING METHOD, MEASURING APPARATUS, ANALYZING APPARATUS, ELLIPSOMETER, AND COMPUTER PROGRAM

(75) Inventors: Nataliya Nabatova-Gabain, Kyoto (JP); Yoko Wasai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 264 days.

(21) Appl. No.: 11/076,400

(22) Filed: Mar. 9, 2005

(65) Prior Publication Data
US 2005/0200845 A1    Sep. 15, 2005

(30) Foreign Application Priority Data
Mar. 11, 2004   (JP) ............................. 2004-069655

(51) Int. Cl.
*G01J 4/00* (2006.01)
(52) U.S. Cl. ...................................... 356/369; 356/630
(58) Field of Classification Search ........ 356/364–369, 356/630–632; 250/225
See application file for complete search history.

(56) References Cited

U.S. PATENT DOCUMENTS

| | | | |
|---|---|---|---|
| 7,167,242 B2 * | 1/2007 | Nabatova-Gabain et al. | 356/369 |
| 7,196,793 B2 * | 3/2007 | Nabatova-Gabain et al. | 356/369 |
| 2005/0253080 A1 * | 11/2005 | Janik | 250/372 |
| 2006/0023213 A1 * | 2/2006 | Funakubo et al. | 356/369 |
| 2007/0121124 A1 * | 5/2007 | Nabatova-Gabain et al. | 356/630 |

FOREIGN PATENT DOCUMENTS

| | | |
|---|---|---|
| JP | 2002-340528 | 11/2002 |
| JP | 2002-340789 | 11/2002 |

* cited by examiner

*Primary Examiner*—Hoa Q. Pham

(57) ABSTRACT

An ellipsometer measures any point of a sample by a first spectrometer and a second spectrometer. The ellipsometer performs analysis based on the measurement results obtained by the first spectrometer, performs analysis based on the measurement results obtained by the second spectrometer, and calculates an approximation formula for approximating the analysis results obtained by the second spectrometer to the analysis results obtained by the first spectrometer. The remaining points of the sample are measured with the second spectrometer, and the results of analysis using the measurement results are corrected based on the approximation formula.

19 Claims, 9 Drawing Sheets

MEASURING METHOD, ANALYZING METHOD, MEASURING APPARATUS, ANALYZING APPARATUS, ELLIPSOMETER, AND COMPUTER PROGRAM

CROSS-REFERENCE TO RELATED APPLICATION

This non-provisional application claims priority under 35 U.S.C. §119(a) on Patent Application No. 2004-69655 filed in Japan on Mar. 11, 2004, the entire contents of which are hereby incorporated by reference.

BACKGROUND OF THE INVENTION

The present invention relates to a measuring method, an analyzing method, a measuring apparatus, an analyzing apparatus, an ellipsometer, and a computer program, capable of reducing the time required for measurement and providing results of required accuracy by performing measurement, or measurement and analysis, for a plurality of points by different methods.

Conventionally, when measuring a plurality of points of one sample, the respective points are often measured one after another by the same method. In this case, since the respective points are measured by the same method, the measurement accuracy at the respective points are usually the same. For example, in the case where polarized light is irradiated to the sample and the polarization state of reflected light is measured by an ellipsometer, the measurement accuracy at the respective points of the sample are almost the same.

Moreover, based on the results of measuring a plurality of points of one sample, the physical properties of each point are sometimes analyzed. In this case, if the same analyzing method is used, the respective points are analyzed with the same accuracy. For example, there is a case where an analyzing computer is connected to an ellipsometer to analyze the film thickness and refractive index of a sample having a thin film, and the composition of the thin film, or other matters. as physical properties. Examples of such an ellipsometer include an ellipsometer that forms a model corresponding to a sample, and executes Various analytical operations by comparing the model and measurement results (see, for example, Japanese Patent Applications Laid Open No. 2002-340789 and No. 2002-340528).

When measuring a plurality of points of a single sample with high accuracy, there is a problem that a long time may require to measure all points because high-accuracy measurement generally takes time. For example, when measuring 50 points of a sample with an ellipsometer, if 5 minutes are required to measure one point, a long time more than 250 minutes is required for the measurements. On the other hand, if the measurement time per point is shortened to reduce the measurement time, the measurement accuracy may sometimes decrease, and therefore it is sometimes difficult to obtain reliable measurement results.

Further, when analyzing a plurality of points of a single sample with high accuracy, similarly to the above measurement, there is a problem that a long time is required for the analysis. For example, if 10 minutes are required to form a model for each point and compare the model with measurement results by the analyzing computer of the ellipsometer, a total of 500 minutes or longer time is required to analyze 50 points of the sample. It is possible to shorten the time required for various operations of analysis, but if the time is shortened, the analysis accuracy may sometimes decrease. Therefore, it seems to be difficult to employ short-time analysis in actual applications. Note that the above-mentioned problems are more noticeable as the number of measurement points and analysis points increases.

BRIEF SUMMARY OF THE INVENTION

The present invention has been made with the aim of solving the above problems, and it is an object of the present invention to provide a measuring method, a measuring apparatus, an ellipsometer and a computer program, capable of providing measurement results of required accuracy within a shorter measurement time, compared to conventional high-accuracy measurements, by combining different measuring methods.

It is another object of the present invention to provide an analyzing method, an analyzing apparatus, an ellipsometer and a computer program, capable of providing analysis results of required accuracy within a shorter analysis time, compared to conventional high-accuracy analysis, by combining different analyzing methods in addition to different measuring methods.

In order to solve the above problems, a measuring method according to a first aspect of the invention is a measuring method for measuring physical properties of a material to be measured, at a plurality of points of the material, with a measuring apparatus capable of performing measurements by a plurality of methods, and characterized by comprising: a first step of measuring any point of the material to be measured; a second step of measuring the same point by a method capable of performing measurement in a shorter time compared to the measurement of the first step; a third step of calculating an approximation formula for approximating measurement results of the second step to measurement results of the first step; a fourth step of measuring the remaining points by the method of the second step; and a fifth step of correcting measurement results of the fourth step, based on the approximation formula.

A measuring method according to a second aspect of the invention is a measuring method in which light is irradiated to a plurality of points of a material to be measured and a change in the state of reflected light is measured for each point with a measuring apparatus capable of performing measurements by a plurality of methods, and characterized by comprising: a first step of irradiating light and measuring any point of the material to be measured; a second step of irradiating light and measuring the same point by a method capable of performing measurement in a shorter time compared to the measurement of the first step; a third step of calculating an approximation formula for approximating measurement results of the second step to measurement results of the first step; a fourth step of irradiating light and measuring the remaining points by the method of the second step; and a fifth step of correcting measurement results of the fourth step, based on the approximation formula.

An analyzing method according to a third aspect of the invention is an analyzing method for analyzing a material to be analyzed, by measuring physical properties of the material at a plurality of points of the material with an analyzing apparatus capable of performing measurement and analysis by a plurality of methods, and characterized by comprising: a first step of measuring any point of the material to be analyzed; a second step of analyzing the same point based on measurement results of the first step; a third step of measuring the same point by a method capable of performing measurement in a shorter time compared to the measurement of the first step; a fourth step of analyzing the same point by a method capable of performing analysis in a shorter time compared to the analysis of the second step, based on measurement results of the third step; a fifth step of calculating an approximation formula for approximating analysis results of the fourth step to analysis results of the second step; a sixth step of measuring the remaining points by the method of the third step; a seventh step of analyzing the remaining points by the method of the fourth step, based on measurement results of the sixth step; and an eighth step of correcting analysis results of the seventh step, based on the approximation formula.

An analyzing method according to a fourth aspect of the invention is an analyzing method for analyzing a material to be analyzed, by measuring physical properties of the material at a plurality of points of the material with an analyzing apparatus capable of performing measurement and analysis by a plurality of methods, and characterized by comprising: a first step of measuring any point of the material to be analyzed; a second step of forming a first model having a plurality of parameters describing the physical properties of the material to be analyzed; a third step of calculating reference values of the material for the same point, based on measurement results of the first step and the first model; a fourth step of measuring the same point by a method capable of performing measurement in a shorter time compared to the measurement of the first step; a fifth step of forming a second model having a smaller number of parameters compared to the first model; a sixth step of calculating first analytical values of the material for the same point, based on measurement results of the fourth step and the second model; a seventh step of calculating an approximation formula for approximating the first analytical values to the reference values; an eighth step of measuring the remaining points by the method of the fourth step; a ninth step of calculating second analytical values of the material for the remaining points, based on measurement results of the eighth step and the second model; and a tenth step of correcting the second analytical values, based on the approximation formula.

An analyzing method according to a fifth aspect of the invention is an analyzing method for analyzing a material to be analyzed, by irradiating light to a plurality of points of the material and measuring a change in the state of reflected light for each point with an analyzing apparatus capable of performing measurement and analysis by a plurality of methods, and characterized by comprising: a first step of irradiating light and measuring any point of the material to be analyzed; a second step of forming a first model having a plurality of parameters describing physical properties of the material to be analyzed; a third step of calculating reference values of the material for the same point, based on measurement results of the first step and the first model; a fourth step of irradiating light and measuring the same point by a method capable of performing measurement in a shorter time compared to the measurement of the first step; a fifth step of forming a second model having a smaller number of parameters compared to the first model; a sixth step of calculating first analytical values of the material for the same point, based on measurement results of the fourth step and the second model; a seventh step of calculating an approximation formula for approximating the first analytical values to the reference values; an eighth step of irradiating light and measuring the remaining points by the method of the fourth step; a ninth step of calculating second analytical values of the material for the remaining points, based on measurement results of the eighth step and the second model; and a tenth step of correcting the second analytical values based on the approximation formula.

A measuring apparatus according to a sixth aspect of the invention is a measuring apparatus for measuring physical properties of a material to be measured, at a plurality of points of the material, and characterized by comprising: first measuring means for measuring any point of the material to be measured; second measuring means for measuring a plurality of points by a method capable of performing measurement in a shorter time compared to the first measuring means; approximation formula calculating means for calculating an approximation formula for approximating results of measuring the same point by the second measuring means to measurement results obtained by the first measuring means; and correcting means for correcting results of measuring the remaining points by the second measuring means, based on the approximation formula.

An analyzing apparatus according to a seventh aspect of the invention is an analyzing apparatus for analyzing a material to be analyzed, by measuring physical properties of the material at a plurality of points of the material, and characterized by comprising: first measuring means for measuring any point of the material to be analyzed; second measuring means for measuring a plurality of points by a method capable of performing measurement in a shorter time compared to the first measuring means; first model forming means for forming a first model having a plurality of parameters describing the physical properties of the material to be analyzed; second model forming means for forming a second model having a smaller number of parameters compared to the first model; reference calculating means for calculating reference values of the material for the same point, based on measurement results obtained by the first measuring means and the first model; first calculating means for calculating first analytical values of the material for the same point, based on results of measuring the same point by the second measuring means and the second model; approximation formula calculating means for calculating an approximation formula for approximating the first analytical values to the reference values; second calculating means for calculating second analytical values of the material for the remaining points, based on results of measuring the remaining points by the second measuring means and the second model; and correcting means for correcting the second analytical values based on the approximation formula.

An ellipsometer according to an eighth aspect of the invention is an ellipsometer for irradiating polarized light to a plurality of points of a material to be measured and measuring a polarization state of reflected light for each point, and characterized by comprising: first measuring means for irradiating light and measuring any point of the material to be measured; second measuring means for irradiating light and measuring a plurality of points by a method capable of performing measurement in a shorter time compared to the first measuring means; approximation formula calculating means for calculating an approximation formula for approximating results of measuring the same point by the second measuring means to measurement results obtained by the first measuring means; and correcting means for correcting results of measuring the remaining points by the second measuring means, based on the approximation formula.

An ellipsometer according to a ninth aspect of the invention is an ellipsometer for analyzing a material to be analyzed, by irradiating polarized light to a plurality of points of the material and measuring a polarization state of reflected light for each point, and characterized by comprising: first measuring means for irradiating light and measuring any point of the material to be analyzed; second measuring means for irradiating light and measuring a plurality of points by a method capable of performing measurement in a shorter time compared to the first measuring means; first model forming means for forming a first model having a plurality of parameters describing physical properties of the material to be analyzed; second model forming means for forming a second model having a smaller number of parameters compared to the first model; reference calculating means for calculating reference values of the material for the same point, based on measurement results obtained by the first measuring means and the first model; first calculating means for calculating first analytical values of the material for the same point, based on results of measuring the same point by the second measuring means and the second model; approximation formula calculating means for calculating an approximation formula for approximating the first analytical values to the reference values; second calculating means for calculating second analytical values of the material for the remaining points, based on results of measuring the remaining points by the second measuring means and the second model; and correcting means for correcting the second analytical values based on the approximation formula.

An ellipsometer according to a tenth aspect of the invention is characterized in that the first measuring means comprises a spectrometer, and the second measuring means comprises a measuring section capable of measuring plurality of wavelengths of light simultaneously.

A computer program according to an eleventh aspect of the invention is a computer program for causing a computer to calculate values concerning measurements at a plurality of points of a material to be measured, and characterized by causing the computer to function as: approximation formula calculating means for calculating an approximation formula for approximating, to first measurement results of any point of the material to be measured, results concerning the same point among second measurement results, based on the first measurement results and the second measurement results of the material to be measured, which were measured in a shorter time compared to the first measurement results; and correcting means for correcting results concerning the remaining points among the second measurement results, based on the approximation formula.

A computer program according to a twelfth aspect of the invention is a computer program for causing a computer to analyze a material to be analyzed, by causing the computer to receive measurement results at a plurality of points of the material, and characterized by causing the computer to function as: first model forming means for forming a first model having a plurality of parameters describing physical properties of the material to be analyzed; second model forming means for forming a second model having a smaller number of parameters compared to the first model; reference calculating means for calculating reference values of the material for any point of the material to be analyzed, based on first measurement results of the same point of the material to be analyzed and the first model; first calculating means for calculating first analytical values of the material for the same point, based on results concerning the same point among second measurement results of the material to be analyzed, which were measured in a shorter time compared to the first measurement results and the second model; approximation formula calculating means for calculating an approximation formula for approximating the first analytical values to the reference values; second calculating means for calculating second analytical values of the material for the remaining points, based on results concerning the remaining points among the second measurement results and the second model; and correcting means for correcting the second analytical values based on the approximation formula.

According to the first, second, sixth and eighth aspects, any point is measured by methods which require different periods of time for the measurement, an approximation formula for approximating measurement results obtained in a shorter time to the other measurement results is calculated, and the results of measuring the remaining points by the short-time method are corrected, based on the approximation formula. Therefore, measurement results with higher accuracy than those of the short-time method can be obtained in a shorter time compared to high-accuracy measurement.

In general, the short-time measuring method makes simple measurements and tends to give lower measurement accuracy compared to long-time measurement. With the present invention, however, since the same point is measured by two methods, namely a measuring method capable of easily obtaining high-accuracy measurement results and a method capable of performing measurement in a shorter time compared to the aforementioned measuring method, it is possible to know the degree of difference between the measurement results obtained by these two methods. Moreover, the present invention calculates an approximation formula for approximating the results of short-time measurement to the results of the method capable of easily obtaining high-accuracy measurement results. Therefore, if it is assumed that the results of short-time measurement of other points differ in the same way as the above-mentioned measurement of the same point, the results of short-time measurement can be corrected by using the approximation formula. In this case, the time taken to measure all points is shortened compared to high-accuracy measurement. Further, with this correction of measurement results, it is possible to obtain measurement results with accuracy close to the results of high-accuracy measurement.

According to the third aspect, in addition to measuring the same point by different methods, the same point is analyzed by different methods, based on the respective measurement results to obtain analysis results; an approximation formula for approximating the difference between the analysis results obtained by these different methods is calculated; and results obtained by measuring and analyzing the remaining points by the methods capable of performing measurement and analysis in a shorter time are corrected, based on the approximation formula. Therefore, analysis results of required accuracy can be obtained in a shorter time compared to high-accuracy measurement and analysis.

According to the fourth, fifth, seventh and ninth aspects of the invention, the first model with a large number of parameters and the second model with a small number of parameters are formed; the same point is analyzed based on both models; and an approximation formula for approximating the analysis results obtained using the second model to the analysis results obtained using the first model is calculated. Therefore, even when the remaining points are analyzed using the second model, it is possible to correct the analysis results by the approximation formula. As a result, it is possible to obtain the analysis results with accuracy close to high accuracy in a shorter time than the time required for high-accuracy analysis, and it is possible to maintain the balance between the analysis accuracy and the analysis time at high level and realize efficient analysis.

According to the tenth aspect, since the first measuring means comprises a spectrometer and the second measuring means comprises a measuring section capable of measuring a plurality of wavelengths simultaneously, the second measuring means can certainly perform measurements in a shorter time compared to the first measuring means. As the measuring section of the second measuring means, it is suitable to use a plurality of photomultipliers, or CCD (Charge Coupled Device), corresponding to measurements of respective wavelengths.

According to the eleventh aspect, by causing a computer to receive measurement results of different methods and calculate an approximation formula for approximating the difference between them, it is possible to correct the results of short-time measurement to improve the accuracy. Hence, even when the remaining points are measured in a short time, the accuracy of the measurement results can be corrected to a required accuracy, thereby contributing to a reduction in the measurement time while achieving the required accuracy.

According to the twelfth aspect, by causing a computer to receive measurement results of different methods and form models with different numbers of parameters, it is possible to perform analysis by two methods of different accuracy levels and calculate an approximation formula for approximating the analysis results, based on the second model having a small number of parameters, to the analysis results, based on the first model having a large number of parameters. In the analysis performed by the computer, the calculation time for the analysis increases with an increase in the number of parameters. However, according to the twelfth aspect, it is possible to correct the results of analysis of the remaining points, based on the second model having a small number of parameters by using the approximation formula that also calculates the calculation time, thereby contributing to providing analysis results with accuracy close to high accuracy as a whole in a short time.

According to the first, second, sixth and eighth aspects, the measurement results with two levels of accuracy are obtained by measuring same point by different methods, and an approximation formula for the respective measurement results obtained by the different measuring methods is obtained. Therefore, it is possible to correct the results of short-time measurement and achieve a balance between the measurement accuracy and the measurement time at high level.

According to the third aspect, an approximation formula is calculated, based on the measurement and analysis results obtained by different methods, and the analysis results of the remaining points are corrected, based on the approximation formula. Consequently, analysis results with accuracy close to high accuracy can be obtained in a short time.

According to the fourth, fifth, seventh and ninth aspects, any point is measured by different methods, and an approximation formula is calculated by forming models with different numbers of parameters and performing analysis. Therefore, the results of analysis of the remaining points, based on the model with a smaller number of parameters, can be corrected using the approximation formula, and it is possible to perform efficient analysis with a good balance between the analysis accuracy and the analysis time.

According to the tenth aspect, since the second measuring means can measure a plurality of wavelengths simultaneously, it can certainly perform measurements in a shorter time compared to the first measuring means.

According to the eleventh aspect, by causing a computer to receive results of different measuring methods and calculate an approximation formula for approximating the difference between these results, it is possible to correct the results of short-time measurement to improve the accuracy and ensure a required measurement accuracy, even when a plurality of points are measured in a short time, thereby contributing to realizing measurements satisfying good measurement accuracy and measurement time.

According to the twelfth aspect, by causing a computer to receive results of different measuring methods and perform analysis, based on models with different numbers of parameters, it is possible to calculate an approximation formula for correcting the analysis results, based on the second model having a smaller number of parameters, and it is possible to obtain analysis results with a required accuracy in a short time, even when a plurality of points are analyzed based on the second model.

The above and further objects and features of the invention will more fully be apparent from the following detailed description with accompanying drawings.

DETAILED DESCRIPTION OF THE INVENTION

The following description will explain in detail the present invention, based on the drawings illustrating an embodiment thereof.

Figure 1:
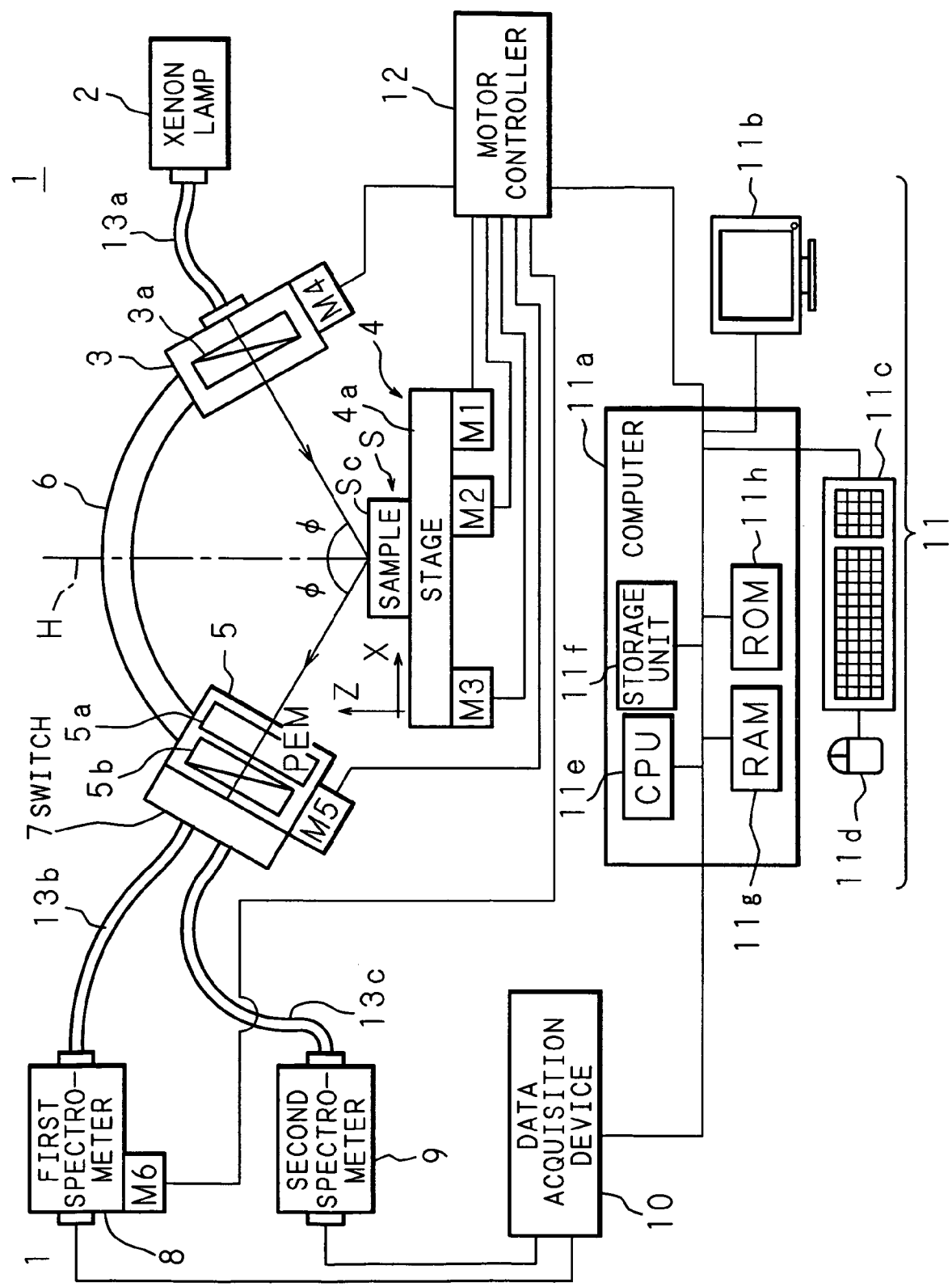
FIG. 1 is an overall block diagram of an ellipsometer according to an embodiment of the present invention.
Figure 2:
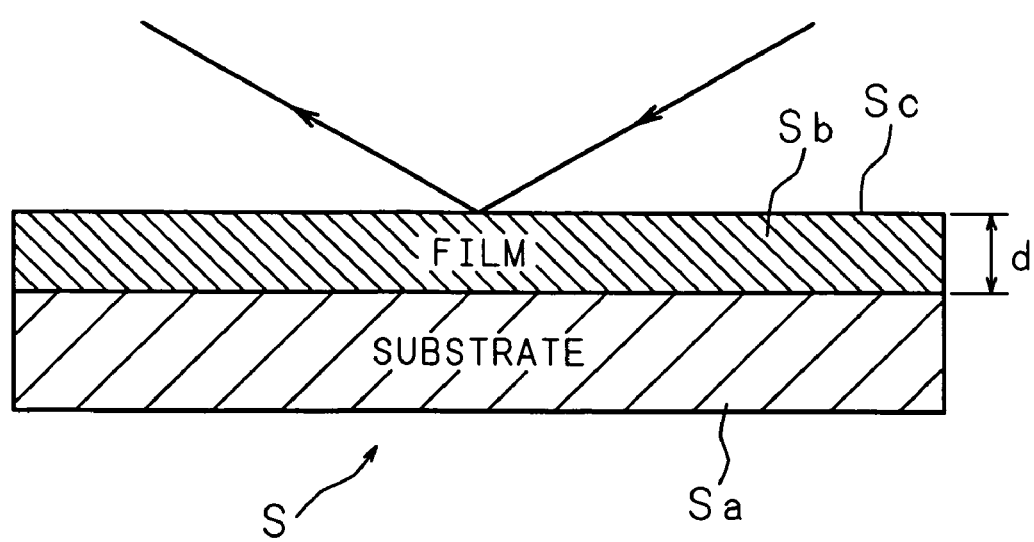
FIG. 2 is a cross sectional view of a sample.

FIG. 1 is a schematic view showing the overall structure of an ellipsometer 1 according to an embodiment of the present invention. The ellipsometer 1 is equivalent to an analyzing apparatus which irradiates polarized light to a sample S (material to be analyzed) comprising a film Sb formed on a substrate Sa as shown in FIG. 2, measures the change polarization state of reflected light, due to the physical properties of the sample S, and analyzes the film thickness d of the film Sb and optical constants (refractive index n, extinction coefficient k), or other matters of the sample S from the measurement results.

The ellipsometer 1 comprises a xenon lamp 2 and a light polarizer 3 connected with a first optical fiber cable 13a, irradiates polarized light to the sample S placed on a stage 4, and receives light reflected from the sample S by a light receiver 5. The light receiver 5 has a switch 7, and the switch 7 is connected to a first spectrometer 8 and a second spectrometer 9 with a second optical fiber cable 13b and a third optical fiber cable 13c, respectively. The polarization state of the light at each wavelength received by the light receiver 5, is measured by either the first spectrometer 8 or the second spectrometer 9. Either the first spectrometer 8 or the second spectrometer 9 transmits the measured polarization state at each wavelength as analog signals to a data acquisition device 10. The data acquisition device 10 converts the analog signals into required values, and a computer 11 analyzes the film thickness and optical constants as the physical properties of the sample S.

A first motor M1 through sixth motor M6 are provided for the stage 4, light polarizer 3, light receiver 5 and first spectrometer 8, and driving of the motors M1-M6 is controlled by a motor controller 12 connected to the computer 11. The motor controller 12 controls the motors M1-M6, based on an instruction outputted from a CPU 11e of the computer 11 as to be described later.

Figure 3A:
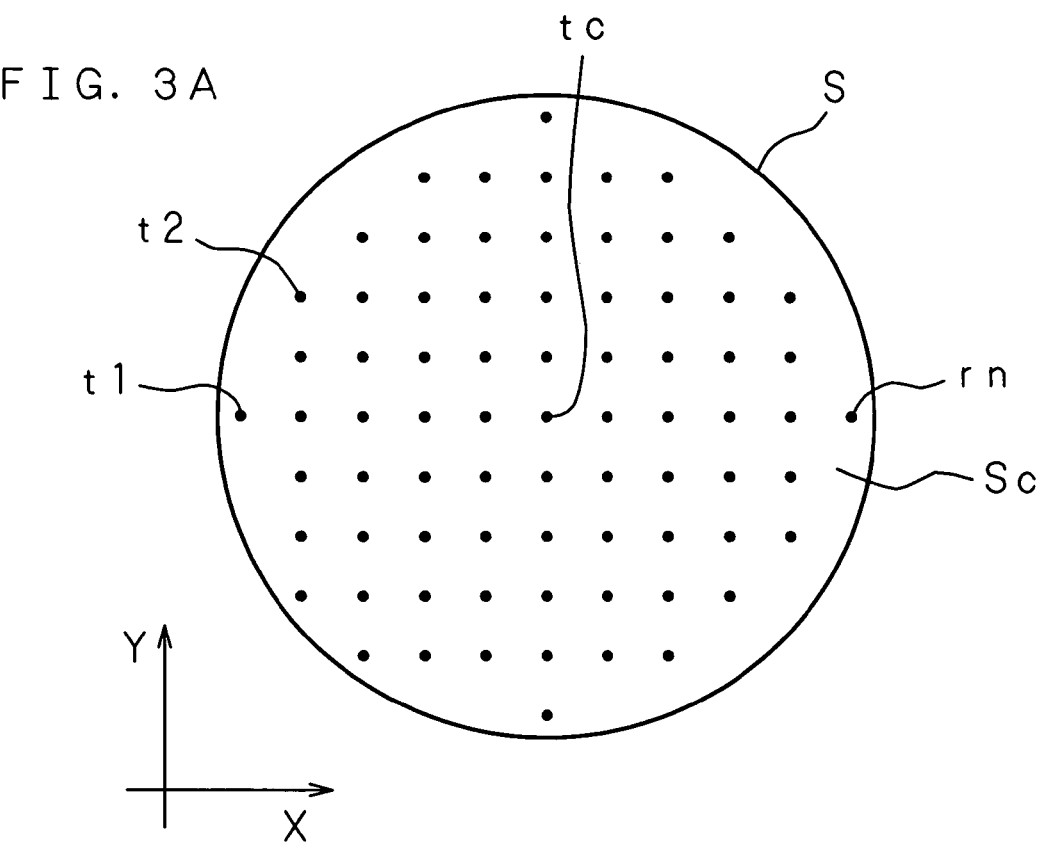
FIG. 3A is a plan view showing a grid configuration of a sample.
Figure 3B:
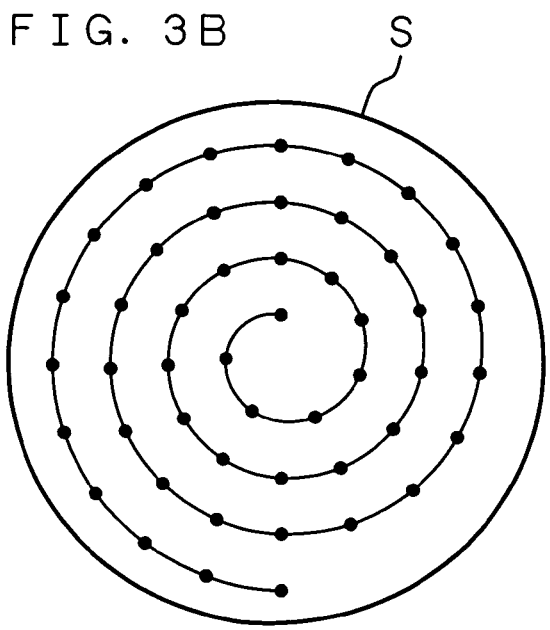
FIG. 3B and FIG. 3C are plan views showing other grid configurations.
Figure 3C:
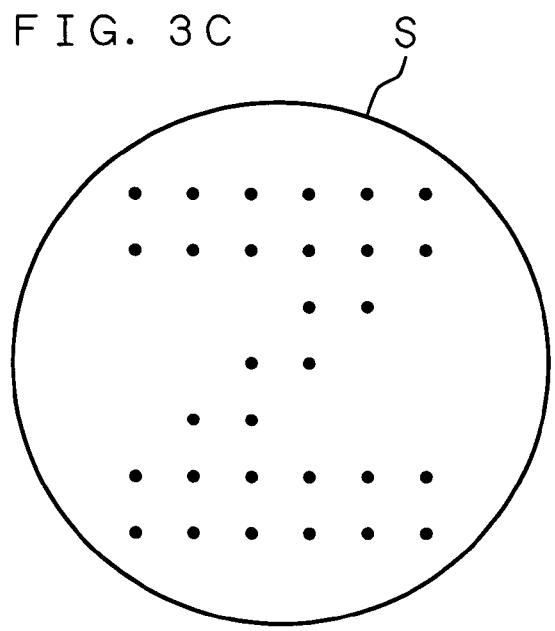

As shown in FIG. 3A, the ellipsometer 1 of this embodiment specifies a plurality of points by the computer 11, as measurement points (hereinafter referred to as the points) on a surface Sc of the sample S, and performs measurement and analysis for the respective points t1 through tn. A collection of points t1 through tn is referred to as a grid. The configuration of the grid is not limited to the form of a lattice shown in FIG. 3A, and the grid may be set in a variety of forms such as a spiral form shown in FIG. 3B and a Z-shaped form shown in FIG. 3C. As the sample S to be analyzed, it is possible to use just a substrate made of materials such as silicon, glass and quartz, or an object prepared by forming a single-layer or multi-layer film Sb (thin film, ultra thin film layer, etc.) on the substrate Sa as shown in FIG. 2.

The xenon lamp 2 of the ellipsometer 1 is a white light source including many wavelength components, and transmits the produced white light to the light polarizer 3 through the first optical fiber cable 13a.

The light polarizer 3 is disposed on a rail 6 in the form of a circular arc, includes a polarizer 3a therein, polarizes the transmitted white light by the polarizer 3a, and irradiates the light to the sample S. When the fourth motor M4 is driven, the light polarizer 3 moves along the rail 6, and this movement enables an adjustment of the angle (incident angle φ) of the irradiated light with respect to a perpendicular line H to the surface Sc of the sample S.

By driving the first motor M1 through the third motor M3, the stage 4 can be moved in the X and Y directions, which cross each other at 90-degrees (see FIG. 1 and FIG. 3A), and in the Z direction that is a height direction, on a stage surface 4a on which the sample S is placed. Thus, by moving the stage 4, the light sequentially strikes the points t1 through tn of the sample S shown in FIG. 3A.

The light receiver 5 is disposed on the rail 6 similarly to the light polarizer 3, incorporates a PEM (Photo Elastic Modulator) 5a and an analyzer 5b, and guides the light reflected from the sample S to the analyzer 5b through the PEM 5a. Moreover, the light receiver 5 can be moved along the rail 6 by the fifth motor M5, and can certainly receive the light reflected from the sample S. The movement of the light receiver 5 is controlled by the motor controller 12 so that the light receiver 5 moves in conjunction with the movement of the light polarizer 3, and the reflection angle φ and the incident angle φ become the same. The PEM 5a in the light receiver 5 obtains elliptical polarization from linear polarization by applying the phase-modulation to the received light at a required frequency (for example, 50 kHz), in order to improve the measurement speed and measurement accuracy. The analyzer 5b transmits a specified polarization among various polarizations phased-modulated by the PEM 5a.

The switch 7 allocates the reflected light received by the light receiver 5 to either the first spectrometer 8 or the second spectrometer 9, based on control by computer 11.

Figure 4:
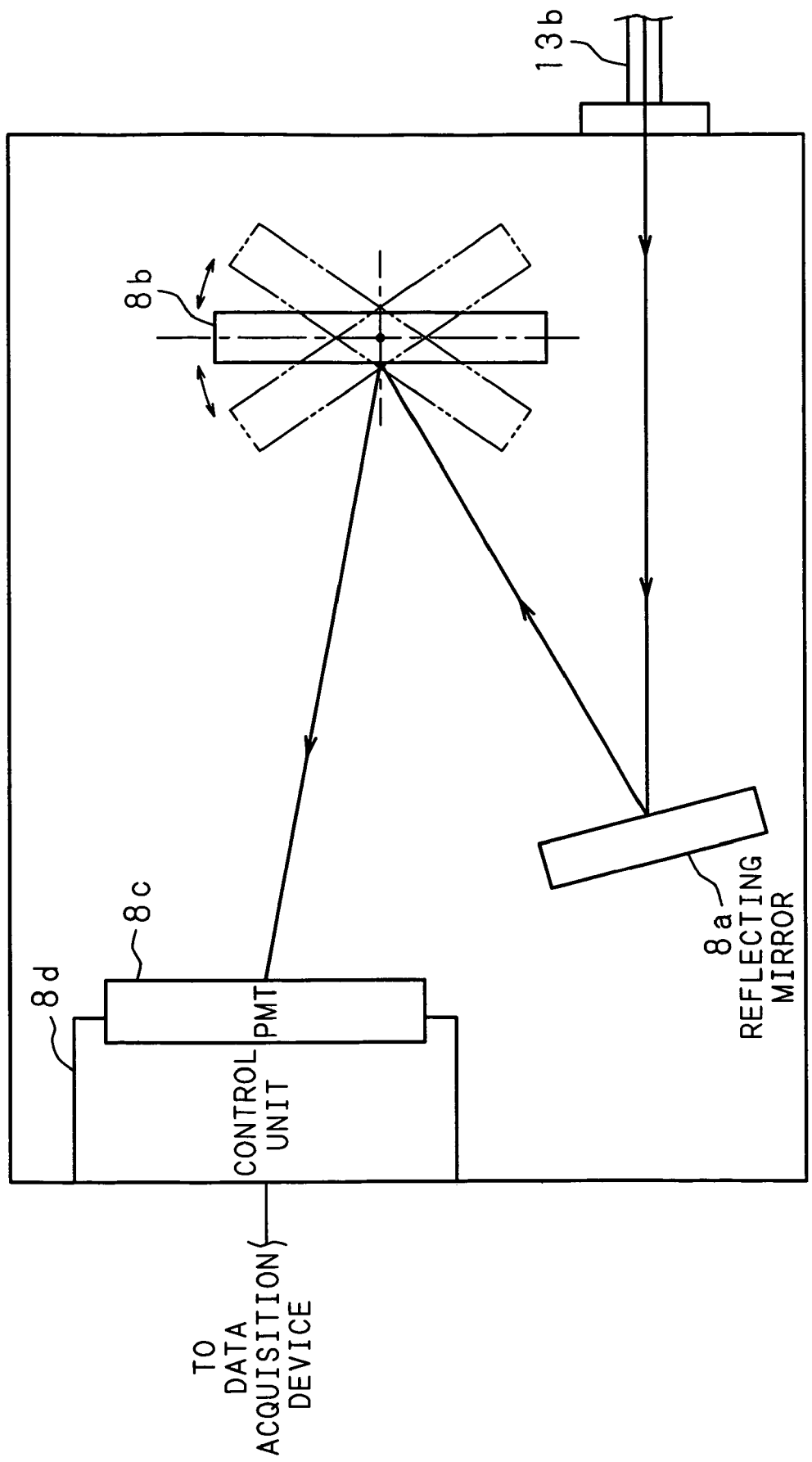
FIG. 4 is a schematic view showing the internal structure of a first spectrometer.

The first spectrometer 8 constitutes first measuring means, comprises a reflecting mirror 8a, a diffraction grating 8b, photomultiplier (PMT) 8c and a control unit 8d as shown in FIG. 4, and guides the light transmitted from the switch 7 to the diffraction grating 8b by reflecting it with the reflecting mirror 8a. The angle of the diffraction grating 8b can be changed by the sixth motor M6 shown in FIG. 1, and the diffraction direction of the guided light is changed by the change of the angle, and therefore it is possible to change the wavelength of emitted light by the diffraction grating 8b. Although not shown in FIG. 4, the present invention uses a sine bar mechanism for mechanically sin-converting the angle of the diffraction grating 8b and showing a dial display so as to numerically display the wavelength corresponding to the changed angle of the diffraction grating 8b. Moreover, it is also possible to use the photomultiplier 8c in combination with a photodiode array (PDA).

The light emitted from the diffraction grating 8b is measured by the PMT 8c, and then the control unit 8d generates an analog signal corresponding to the measured wavelength and transmits it to the data acquisition device 10. Thus, since the first spectrometer 8 measures the each wavelength by varying the angle of the diffraction grating 8b, the measurement takes a long time, but the measurement accuracy is high. As a result, the first spectrometer 8 can perform measurements by changing the wavelengths range and increment according to the film thickness, and, for example, can change the wavelength by small steps, if the film's thickness is thick.

Figure 5:
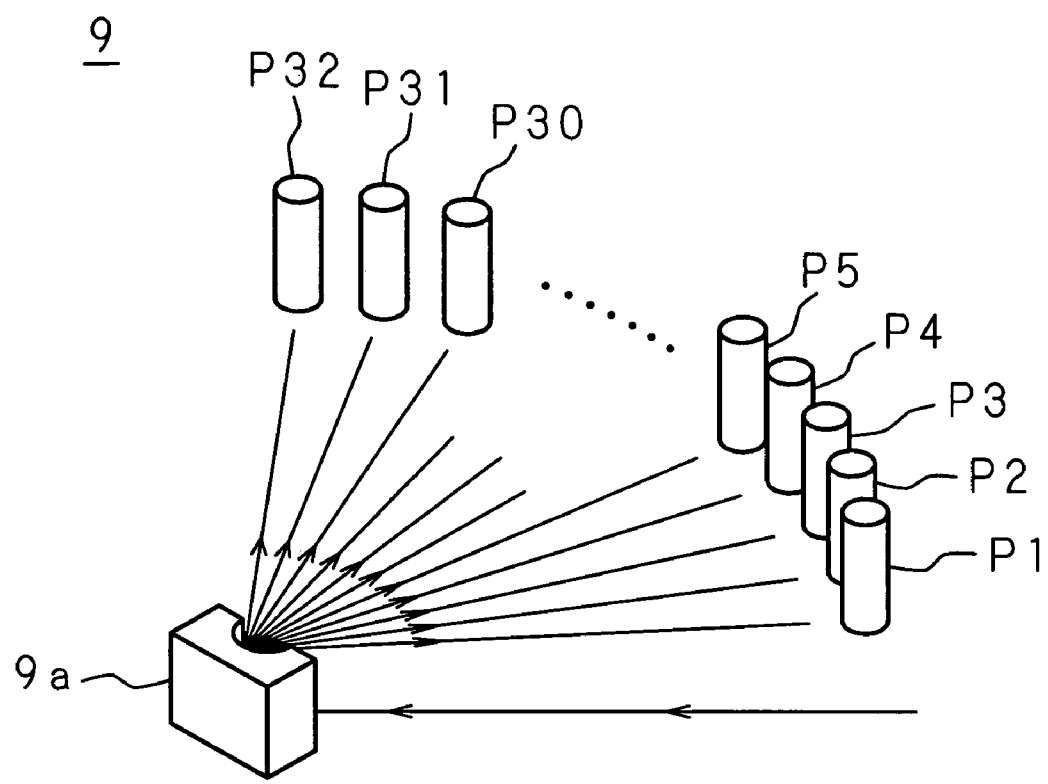
FIG. 5 is a schematic view showing the internal structure of a second spectrometer.

FIG. 5 shows the schematic structure of the second spectrometer 9 constituting second measuring means. The second spectrometer 9 comprises a total of 32 photomultipliers P1 through P32, corresponding to the measuring section, which are disposed in a fan-like form with a diffraction grating 9a at the center. The diffraction grating 9a reflects the light guided through the switch 7 and a mirror (not shown) toward the photomultipliers P1-P32, and allocates a reflection direction according to the each wavelength of light at the time of reflection.

Each of the photomultipliers P1-P32 performs measurement for a specified wavelength reflected by the diffraction grating 9a, and the second spectrometer 9 can simultaneously measure 32 channels, because it has a total of 32 photomultipliers P1-P32. Thus, since the second spectrometer 9 measures a plurality of wavelengths simultaneously, it shortens the measurement time compared to the first spectrometer 8, but the measurement accuracy is lower compared to the first spectrometer 8, because the number of wavelengths to be measured is only 32. Note that signals concerning the contents measured by the photomultipliers P1-P32 are transmitted to the data acquisition device 10.

The data acquisition device 10 calculates the phase difference $\Delta$ and amplitude ratio $\psi$ of the polarization states (p polarization, s polarization) of measured reflected light, based on the signals from the respective spectrometers 8 and 9, and transmits the calculation results to the computer 11. The phase difference $\Delta$ and amplitude ratio $\psi$ establish the relationship shown by equation (1) below, with a complex Fresnel reflection coefficient Rp of p-polarized light and a complex Fresnel reflection coefficient Rs of s-polarized light.

$$Rp/Rs = \tan \psi \cdot \exp(i \cdot \Delta) \quad (1)$$

where i is an imaginary unit (also applied to the following description). Further, Rp/Rs is referred to as a ratio of complex Fresnel reflection coefficient ρ.

The computer 11 comprises a computer main body 11a, a display 11b, a keyboard 11c, a mouse lid, etc. The computer main body 11a includes therein a CPU 11e, a storage unit 11f, a RAM 11g and a ROM 11h connected with an internal bus. The CPU 11e performs later-described various processing according to various computer programs stored in the storage unit 11f. The RAM 11g temporarily stores various data related to the processing, and the ROM 11h stores the contents concerning the functions of the computer 11. In addition to various computer programs, the storage unit 11f stores known data related to the process of manufacturing the sample S, the past data (parameters) about optical constants related to the analysis, and the inputted item data.

If the complex refractive indices of the ambient of the sample S and the substrate Sa are known, the computer 11 of this embodiment calculates the film thickness d of the film Sb and the complex refractive index N of the film Sb by using a modeling program pre-stored in the storage unit 11f from the phase difference Δ and amplitude ratio ψ calculated by the data acquisition device 10. In the case where the sample S consists only of a substrate, the computer 11 calculates the complex refractive index $N_0$ of the substrate. It should be noted that, when n represents the refractive index of the sample S and k represents the extinction coefficient, the complex refractive index N can be calculated from the following optical expression (2):

$$N = n - ik \quad (2)$$

Further, if the wavelength of light, irradiated by the light polarizer 3, is denoted as λ, the phase difference Δ and amplitude ratio ψ calculated by the data acquisition device 10, establish the relationship shown in equation (3) below with the film thickness d, refractive index n, and extinction coefficient k.

$$(d, n, k) = F(\rho) = F(\psi(\lambda, \phi), \Delta(\lambda, \phi)) \quad (3)$$

Measured spectra ($\psi_E(\lambda_i)$, $\Delta_E(\lambda_i)$), calculated from the change in the polarization state of light reflected from the film Sb contain all information about the refractive index n and extinction coefficient k of the substrate Sa and information about the film thickness d, refractive index n and extinction coefficient k of the film Sb, but a single combination of the refractive index n and extinction coefficient k of the substrate Sa and the film thickness d, refractive index n and extinction coefficient k of the film Sb, cannot be calculated from the above measured spectra. Therefore, the computer 11 performs the process of finding a single combination by forming a model, using the information about the refractive index n and extinction coefficient k of the substrate Sa and the information about the film thickness d, refractive index n and extinction coefficient k of the film Sb.

The computer 11 forms a model similar to the material structure of the sample S as shown in FIG. 2 and FIG. 3A, and more specifically, forms a model using data of the items such as the optical constants (refractive index n, extinction coefficient k) of the substrate Sa (for example, silicon), the film thickness d and the optical constants (refractive index n, extinction coefficient k) of the film Sb, as a plurality of parameters describing the physical properties of the sample S. In this embodiment, the computer 11 forms two types of models for the central point Tc shown in FIG. 3A. The two types of models are a first model having a plurality of parameters and a second model having a smaller number of parameters compared to the first model.

Further, in order to minimize the difference between model spectra ($\psi_M(\lambda_i)$, $\Delta_M(\lambda_i)$) theoretically obtained from the first model for the point Tc, by using the film thickness and a dispersion formula, which represents the wavelength dependence of the film's dielectric constant, and the measured spectra ($\psi_E(\lambda_i)$, $\Delta_E(\lambda_i)$) concerning the measurement results of the first spectrometer 8, the computer 11 changes the film thickness and the parameters of the dispersion formula, and performs the analytical process of finding the refractive index n and the extinction coefficient k, by changing the film thickness d and the parameters of dispersion formula, till the difference between these spectra is minimized. Note that this analytical process can also be performed using references (known table data), the past measured data, the optical constants of a single-layer thin film of a material similar to the sample S, or other matters, instead of using the dispersion formula.

The dispersion formula represents the wavelength-dependency of the dielectric constant of the material, wherein the dielectric constant ε (λ) can be determined in the optical range between near infrared light and ultraviolet light based upon the atomic structure of the material. Known examples of dispersion formulas include a formula based on classical physics (a harmonic oscillator), a formula based on quantum mechanics, an empirical formula, and the like, which generally include two or more parameters. The model is applied to the measured data by adjusting all the unknown values (thickness of each layer, parameters of the dispersion formula, volume fractions of material's components, or the like) included in the aforementioned model. This processing is referred to as "fitting", wherein the thickness, parameters of dispersion formula, the volume fractions, and the like, of each layer are obtained. The dielectric constant ε (λ) of the material can be calculated from the parameters of the dispersion formula, based upon the fitting results. The relation between the dielectric constant of the material and the refractive index is represented by the following expression.

$$\epsilon = N^2 \quad (4)$$

Now, brief description will be made regarding fitting operation frequently employed in methods according to the present invention.

With the set of T pairs of measured (experimental) data as Exp(i=1,2, and so on through T), and with the set of T pairs of the data calculated using the model as Mod(i=1,2, and so on through T), making assumption that error of measurement follows normal distribution, and with the standard deviation as σi, the mean square error ($\chi^2$) is represented by the expression.

$$x^2 = [1/(2T - P)] \sum_{i=1}^{T} (\text{Exp}_i - \text{Mod}_i)^2 / \sigma_i^2 \quad (5)$$

Moreover, the computer 11 performs an analytical process similar to the above-mentioned content for the point tc by using model spectra theoretically obtained from the second model and the measured spectra related to the measurement results of the second spectrometer 9, and then performs the process of calculating an approximation formula approximating the result obtained by this analytical process to the result of analysis, based on the first model and the measurement results of the first spectrometer 8.

Further, the computer 11 uses the second model for points other than the central point tc, and performs an analytical process similar to the above, by using the model spectra theoretically obtained from the second model and the measured spectra related to the measurement results of the second spectrometer 9, for the points other than the central point tc, and then corrects the results of this analytical process, based on the calculated approximation formula. In this manner, the analysis results, with accuracy close to the accuracy of analysis using the measurements made by the first spectrometer 8, are obtained in a short time.

A sequence of steps performed by the computer 11 is prescribed in the first computer program for analysis, stored in the storage unit 11f, and the first computer program includes the following plurality of contents.

In order to cause the CPU 11e of the computer 11 to function as first model forming means, the first computer program includes content that causes the CPU 11e to form the above-mentioned first model for any point (the central point tc in this embodiment) of the sample S to be measured. Moreover, in order to cause the CPU 11e of the computer 11 to function as second model forming means, the first computer program includes content that causes the CPU 11e to form the above-mentioned second model for the central point tc.

Further, in order to cause the CPU 11e of the computer 11 to function as reference calculating means, the first computer program includes content that causes the CPU 11e to calculate reference values for the film thickness d and the optical constants (n, k) for any point (point tc) of the sample S, based on the results of measuring same point (the central point tc) of the sample S, to be measured, by the first spectrometer 8, as the first measurement results and the first model, by the analytical process using the above-mentioned dispersion formula.

Additionally, in order to cause the CPU 11e of the computer 11 to function as first calculating means, the first computer program includes content that causes the CPU 11e to calculate first analytical values for the film thickness d and the optical constants (n, k), based on the results of any point (point tc) among results obtained based on measurements of the same points t1 through tn of the sample S, by the second spectrometer 9 as the second measurement results and the second model, by the analytical process using the above-mentioned dispersion formula. Besides, in order to cause the CPU 11e of the computer 11 to function as approximation formula calculating means, the first computer program includes content that causes the CPU 11e to calculate an approximation formula for approximating the calculated first analytical values to the reference values.

Moreover, in order to cause the CPU 11e of the computer 11 to function as second calculating means, the first computer program includes content that causes the CPU 11e to calculate second analytical values for the film thickness d and the optical constants (n, k), based on the results of respective points other than the point tc among the second measurement results and the second model, by the analytical process using the dispersion formula. Note that the same number of second analytical values as the number of points excluding the point tc are present. Finally, in order to cause the CPU 11e of the computer 11 to function as correcting means, the first computer program includes content that causes the CPU 11e to calculate correction values, by correcting the calculated second analytical values, based on the approximation formula.

In addition, the storage unit 11f of the computer 11 stores a second computer program for measurement. The second computer program prescribes content that causes the computer 11 to drive the motors M1-M6, control the switch 7, etc. according to each measurement stage. For example, in order to measure the point tc of the sample S, the second computer program prescribes content that causes the CPU 11e to output to the motor controller 12 an instruction to set the reflection angle $\phi$ and incident angle $\phi$ at required angles by driving the fourth motor M4 and fifth motor M5, and move the stage 4 by driving the first motor M1 through third motor M3 so that the light irradiated from the light polarizer 3 strikes the point tc. The second computer program also prescribes content that causes the CPU 11e to output to the switch 7 an instruction that instructs the switch 7 to guide the light received by the light receiver 5 to the first spectrometer 8. Further, the second computer program prescribes content that causes the CPU 11e to output to the motor controller 12 an instruction to drive the sixth motor M6 of the first spectrometer 8 at a required angle when the switch 7 guides the light to the first spectrometer 8. Note that the first spectrometer 8 measures the received light at each wavelength by appropriately driving the sixth motor M6.

Moreover, the second computer program also prescribes content that causes the CPU 11e to output to the motor controller 12 an instruction to drive the first motor M1 through third motor M3 so that light sequentially strikes the points tc, t1, t2 through tn of the sample S, when the first spectrometer 8 has finished the measurement according to the instruction. In accordance with this content, the second computer program also prescribes content to output an instruction to the switch 7 to guide the light received by the light receiver 5 to the second spectrometer 9.

The storage section 11f of the computer 11 also stores a computer program for display to display the current processing state, analysis results, etc. on the display 11b, in addition to the first and second computer programs.

Further, the computer 11 can set various items concerning measurement and analysis, and various items of parameters for model formation with the keyboard 11c or mouse 11d shown in FIG. 1, and also allows the respective devices 3, 5 and 7 to be moved manually using the keyboard 11c or mouse 11d.

Figure 6:
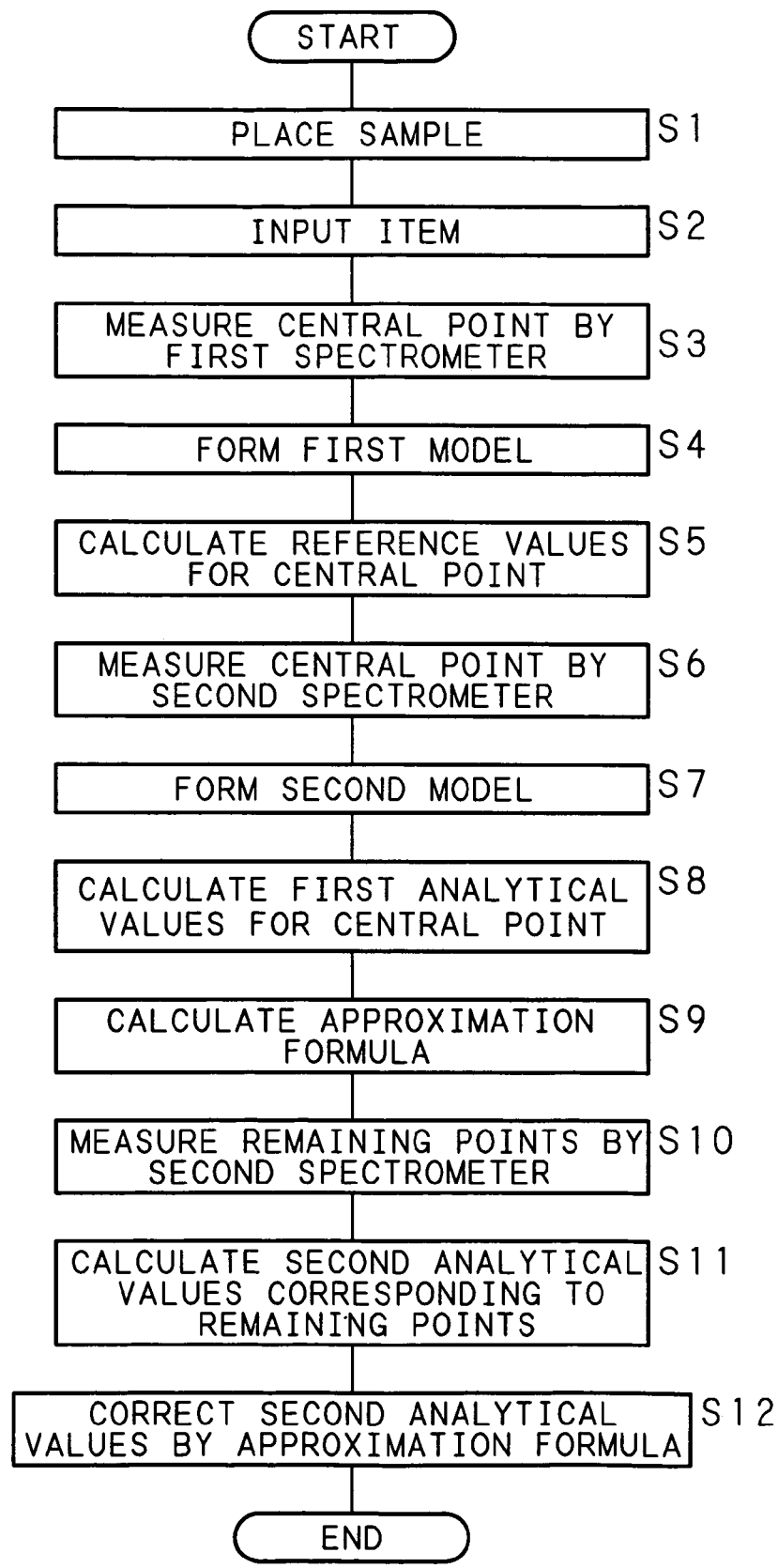
FIG. 6 is a first flowchart showing the overall processing steps of an analyzing method using an ellipsometer.

Next, referring to the first flowchart shown in FIG. 6, the following description will explain a sequence of processing steps of the methods of measuring and analyzing the sample S with the ellipsometer 1.

First, the sample S is placed on the stage 4 of the ellipsometer 1 (S1). Next, respective items, such as the coordinate positions of points t1 through tn of sample S to be measured, incident angle $\phi$, parameters necessary for the formation of each model, and the tolerance range of mean square error, are inputted into the computer 11 as the items related to analysis (S2). At this preparation stage, the switch 7 is set to guide the light to the first spectrometer 8.

The ellipsometer 1 moves the light polarizer 3 and light receiver 5 so that the incident angle $\phi$ and reflection angle $\phi$ become the inputted numerical values, moves the stage 4, and irradiates polarized light to the central point tc among the points t1 through tc of the set grid so as to measure the polarization state of reflected light received by the light receiver 5 at each wavelength with the first spectrometer 8 (S3). Based on the results of measurement performed by the first spectrometer 8, the data acquisition device 10 calculates measured spectra ($\psi_E(\lambda_i)$, $\Delta_E(\lambda_i)$) concerning the phase difference $\Delta$ and amplitude ratio $\psi$ at each wavelength, and outputs the calculation results to the computer 11.

Next, the ellipsometer 1 forms the first model with the computer 11 by using the items inputted for the central point tc and the data (parameters) stored in the storage unit $11f$ (S4). Then, the computer 11 of the ellipsometer 1 calculates the reference values for the film thickness d, refractive index n and extinction coefficient k for the central point tc by the process of fitting the film thickness and the parameters of the dispersion formula so as to minimize the mean square error $\chi_2$ of the above-mentioned equation (5), based on the measured spectra ($\psi_E(\lambda_i)$, $\Delta_E(\lambda_i)$) obtained by the measurements, made by the first spectrometer 8 and model spectra ($\psi_M(\lambda_i)$, $\Delta_M(\lambda_i)$) theoretically obtained from the first model (S5).

Figure 7:
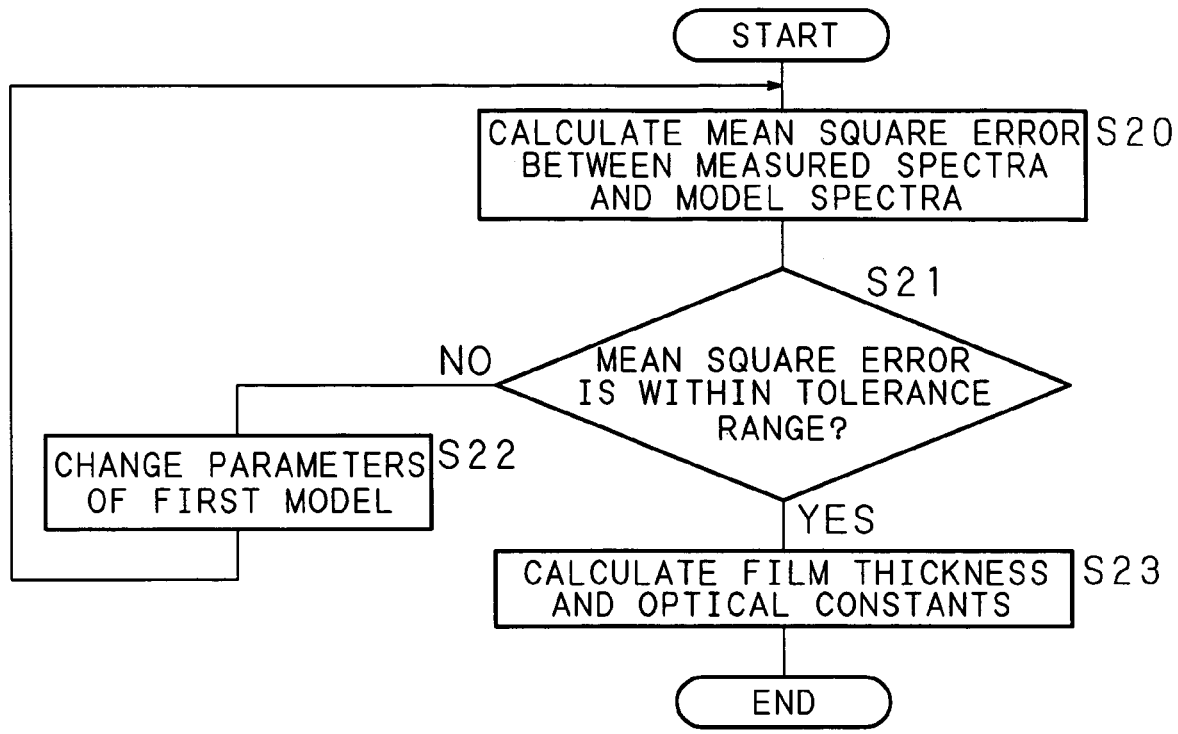
FIG. 7 is a second flowchart showing the procedure for finding a film thickness and optical constants.

Specific contents of the process of calculating the reference values (S5) are described in the second flowchart of FIG. 7. First, the computer 11 calculates the mean square error between the measured spectra and the model spectra based on the above-mentioned equation (5) (S20), and then judges whether or not the calculated mean square error is within the initially set tolerance range (S21). If the mean square error is not within the tolerance range (S21: NO), the computer 11 changes the contents of the parameters describing the formed first model (S22), returns to the stage of calculating the mean square error between the measured spectra and the model spectra (S20), and then repeats the above-mentioned processing (S20 through S22) until the mean square error falls within the tolerance range. When the mean square error falls within the tolerance range (S22: YES), the computer 11 calculates the film thickness d and optical constants (refractive index n, extinction coefficient k) as the reference values, based on the contents of the respective spectra at this time and the parameters of the dispersion formula (S23).

Let's move back to the first flowchart of FIG. 6 to continue the explanation. Next, the ellipsometer 1 switches the switch 7 to guide the light to the second spectrometer 9, and performs measurement for the central point tc by the second spectrometer 9 (S6). Since the second spectrometer 9 measures 32 types of wavelengths simultaneously as shown in FIG. 5, the time required for measurement by the second spectrometer 9 is significantly shortened compared to the measurement time of the first spectrometer 8. The data acquisition device 10 calculates measured spectra for each wavelength, based on the results of measurements made by the second spectrometer 9, and outputs the results to the computer 11.

Then, the ellipsometer 1 causes the computer 11 to form a second model having a smaller number of parameters compared to the first model for the central point tc (S7), and calculate the first analytical values for the film thickness d and optical constants (n, k) according to the processing contents shown in the second flowchart of FIG. 7, based on the model spectra for the second model and the measured spectra obtained by the measurements made by the second spectrometer 9 (S8). Moreover, the ellipsometer 1 calculates an approximation formula for approximating the calculated first analytical values to the reference values by the computer 11 (S9).

Further, the ellipsometer 1 measures the remaining points t1 through tn other than the central point tc one after another with the second spectrometer 9 (S10), and the computer 11 obtains the measured spectra for each wavelength corresponding to the respective points. In addition, the computer 11 uses the second model formed at the previous stage (S7) and calculates the second analytical values corresponding to the remaining points, based on the model spectra of the second model and the measured spectra for the respective points (S11). Finally, the computer 11 corrects the respective second analytical values by using the above-mentioned approximation formula (S12).

Thus, the ellipsometer 1 according to this embodiment obtains an approximation formula by measuring and analyzing one point by two methods of different accuracy levels, measures the remaining points by the low-accuracy method capable of performing measurements in a short time, uses the second model obtained at the previous stage to shorten the time taken for the measurement and analysis, and corrects the second analytical values by the approximation formula to improve the accuracy of the analysis results. Consequently, the ellipsometer 1 achieves a balance between the time taken for measurement and analysis and the accuracy of analysis results at high level. Note that it may also be possible to input the first model and second model formed in advance into the computer 11. In this case, the processes of forming the first model (S4) and the process of forming the second model (S7) in the first flowchart of FIG. 6 can be omitted, thereby further facilitating the automation of a sequence of processing steps.

The ellipsometer 1 according to this embodiment is not limited to the above-mentioned form, and can be applied in a variety of modified forms. For example, the point to be measured and analyzed to find the approximation formula is not limited to the central point tc, and it may also be possible to use other point, or a plurality of points. Moreover, although the PEM 5a is disposed inside the light receiver 5 as shown in FIG. 1, it may be placed just after the polarizer 3a in the light polarizer 3. Further, the second spectrometer 9 may simultaneously perform measurements for a plurality of wavelengths by using a CCD (Charge Coupled Device) in place of the photomultipliers P1-P32.

In addition, it may also be possible to omit the analytical process concerning the formation of models and perform only measurement with the ellipsometer 1. In such a modified example of the ellipsometer, for example, the computer 11 calculates an approximation formula for approximating the measurement results (measured spectra) obtained by the second spectrometer 9 to the measurement results (measured spectra) obtained by the first spectrometer 8 for the central point tc, and corrects the measurement results of the remaining points obtained by the second spectrometer 9, based on the approximation formula.

Figure 8:
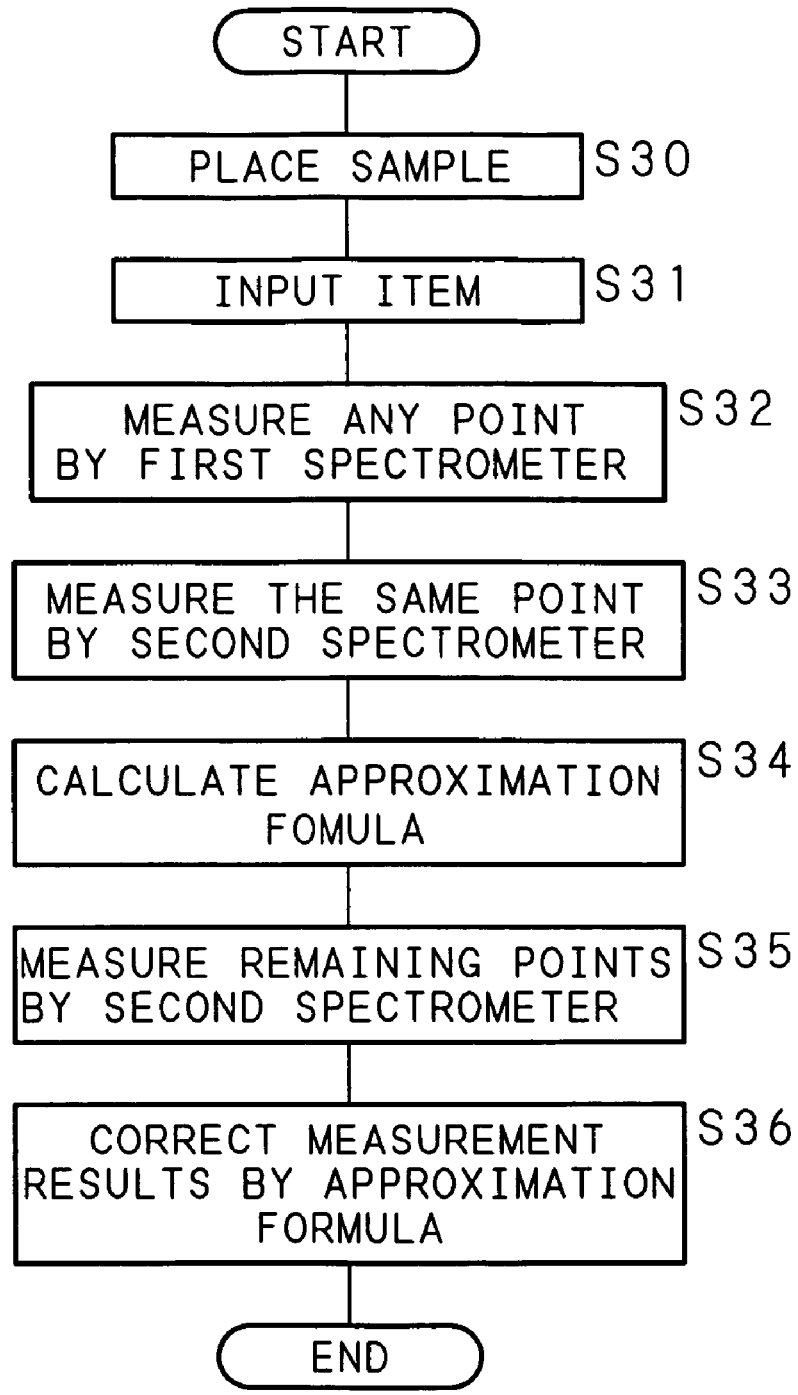
FIG. 8 is a third flowchart showing the processing steps of a measuring method of the present invention.

The processing performed by such an ellipsometer that performs only measurement includes the steps shown in the third flowchart of FIG. 8. Specifically, first, the sample S (corresponding to a material to be measured) is placed on the stage 4 (S30), and items concerning measurement are inputted into the computer 11 (S31). The first spectrometer 8 performs measurement for any point (for example, the point tc) (S32), the second spectrometer 9 performs measurement for the same point (S33), and the computer 11 calculates an approximation formula for approximating the measurement results obtained by the second spectrometer 9 to the measurement results obtained by the first spectrometer 8 (S34). Moreover, the second spectrometer 9 performs measurement for the remaining points (S35), and corrects the measurement results by the approximation formula (S36). With such a measuring method, the measurement time can be shortened compared to a method in which all points are measured by the first spectrometer 8, and the results obtained by making the correction have higher accuracy compared to the results measured by the second spectrometer 9, and thus it is possible to achieve a good balance between the measurement time and the measurement accuracy.

Further, it may also be possible to omit the switch 7 and perform measurement only by either the first spectrometer 8 or the second spectrometer 9 in the ellipsometer 1 shown in FIG. 1. The processing steps performed in this structure are as follows. In the case, where measurement is performed for some point (for example, the point tc), first, measurement is performed by setting the incident angle φ and reflection angle φ at an angle showing the greatest sensitivity for the sample S (Brewster angle, for example, about 76 degrees if the sample S is silicon), and then measurement is performed by setting the incident angle φ and reflection angle φ at a different angle (about 75 degrees) from the above-mentioned angle.

Such a method in which measurement is performed by changing the incident angle is also applicable to the ellipsometer 1 comprising two spectrometers 8 and 9 shown in FIG. 1, and an ellipsometer that performs only measurement.

For the above-mentioned measurement, it is preferable to set an incident angle φ (for example, about 76 degrees) showing the greatest sensitivity for the sample S. However, in the structure of the ellipsometer 1, when setting an optimum incident angle for the sample S, the light polarizer 3 and the stage 4 sometimes interfere and prevent setting of the optimum incident angle. In this case, by performing the measurement for some point and correcting the respective measurement results by using the approximation formula as described above, it is possible to improve at least the measurement accuracy.

Moreover, the content of the present invention is applicable not only to ellipsometers, but also to measuring apparatuses and analyzing apparatuses that perform measurement by irradiating light, and to measuring apparatuses and analyzing apparatuses that perform measurement by using a plurality of methods. In addition, the present invention is also applicable to analyzing apparatuses that perform analysis using a method in which models are not formed.

Figure 9:
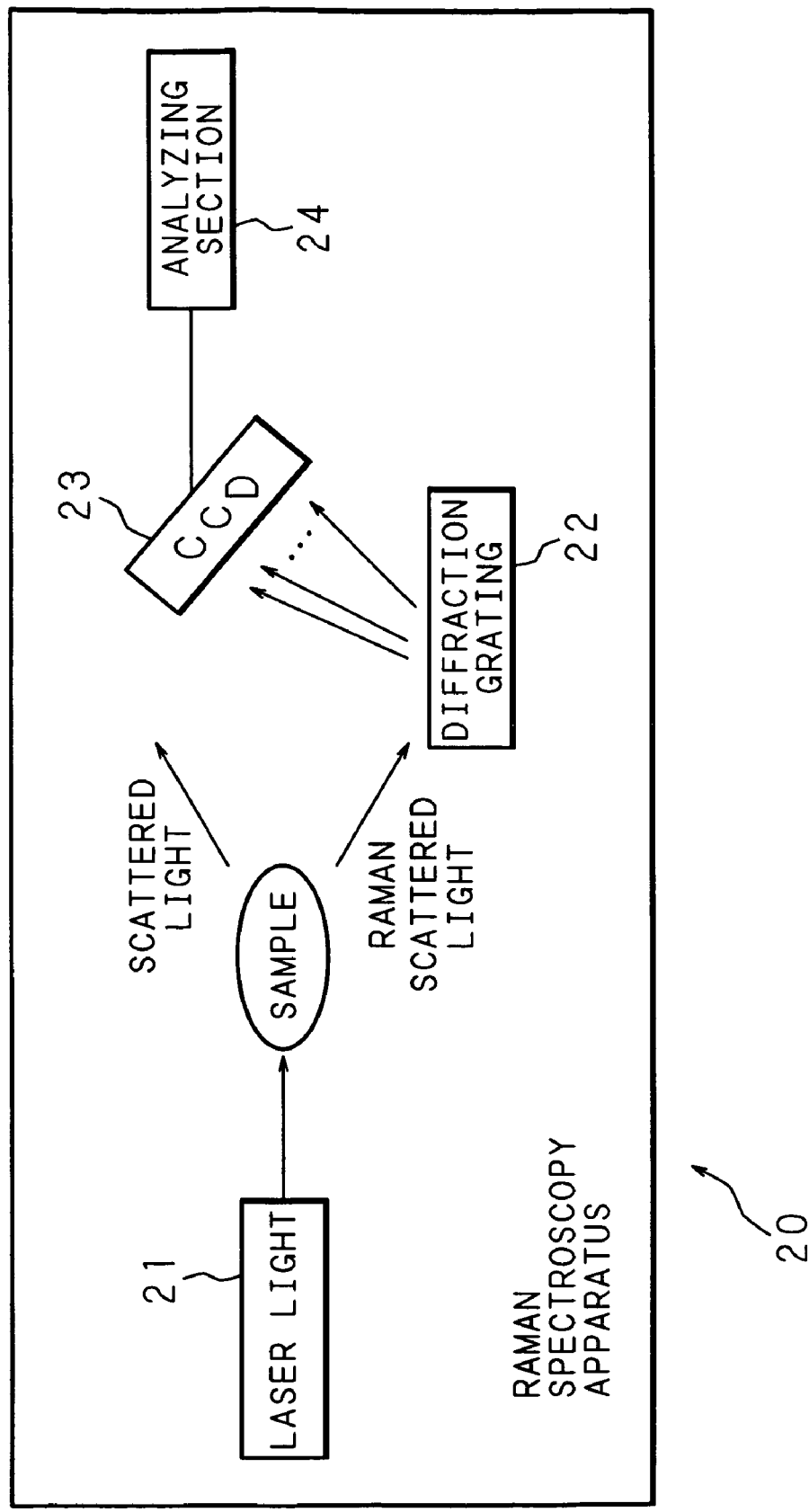
FIG. 9 is a schematic block diagram of a Raman spectroscopy apparatus according to the present invention.

For example, with a Raman spectroscopy apparatus 20 shown in FIG. 9, by performing measurement and analysis using a plurality of methods, it is possible to efficiently analyze the waveform separation. The Raman spectroscopy apparatus 20 of FIG. 9 is a device for performing measurement by irradiating laser light, and comprises a laser light source 21 for irradiating laser light toward a sample, a diffraction grating 22 for separating the Raman scattered light in the scattered light from the sample, a CCD 23 for converting the separated light of each wavelength into an electric signal, and an analyzing section 24 for performing waveform separation from the converted electric signals.

With such a Raman spectroscopy apparatus 20, two types of measurement which take different periods of time for the measurement are performed by adjusting the state of laser light irradiated to a part of the sample, and two types of analysis which take different period of time for the analysis are performed with an analyzing section 24, based on the respective measurement results, so as to calculate an approximation formula for approximating one analysis result to the other analysis result. After calculating the approximation formula, the remaining points are measured by the method capable of performing measurement in a shorter time and analyzed, and then the results are corrected based on the approximation formula, thereby enabling analysis capable of maintaining the balance between the analysis accuracy and the analysis time at high level.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A measuring method for measuring physical properties of a material to be measured, at a plurality of points of the material, with a measuring apparatus capable of performing measurements by a plurality of methods, comprising:
   a first step of measuring any point of the material to be measured;
   a second step of measuring the same point by a method capable of performing measurement in a shorter time compared to the measurement of the first step;
   a third step of calculating an approximation formula for approximating measurement results of the second step to measurement results of the first step;
   a fourth step of measuring the remaining points by the method of the second step;
   a fifth step of correcting measurement results of the fourth step, based on the approximation formula; and
   a step of displaying the corrected results of the fifth step on a display.

2. A measuring method in which light is irradiated to a plurality of points of a material to be measured, and a change in the state of reflected light is measured for each point with a measuring apparatus capable of performing measurements by a plurality of methods, said measuring method comprising:
   a first step of irradiating light and measuring any point of the material to be measured;
   a second step of irradiating light and measuring the same point by a method capable of performing measurement in a shorter time compared to the measurement of the first step;
   a third step of calculating an approximation formula for approximating measurement results of the second step to measurement results of the first step;
   a fourth step of irradiating light and measuring the remaining points by the method of the second step;
   a fifth step of correcting measurement results of the fourth step, based on the approximation formula; and
   a step of displaying the corrected results of the fifth step on a display.

3. An analyzing method for analyzing a material to be analyzed by measuring physical properties of the material at a plurality of points of the material with an analyzing apparatus capable of performing measurement and analysis by a plurality of methods, said analyzing method comprising:
   a first step of measuring any point of the material to be analyzed;
   a second step of analyzing the same point based on measurement results of the first step;
   a third step of measuring the same point by a method capable of performing measurement in a shorter time compared to the measurement of the first step;
   a fourth step of analyzing the same point by a method capable of performing analysis in a shorter time compared to the analysis of the second step, based on measurement results of the third step;
   a fifth step of calculating an approximation formula for approximating analysis results of the fourth step to analysis results of the second step;
   a sixth step of measuring the remaining points by the method of the third step;

a seventh step of analyzing the remaining points by the method of the fourth step, based on measurement results of the sixth step;

an eighth step of correcting analysis results of the seventh step, based on the approximation formula; and a step of displaying the corrected results of the eighth step on a display.

4. An analyzing method for analyzing a material to be analyzed by measuring physical properties of the material at a plurality of points of the material with an analyzing apparatus capable of performing measurement and analysis by a plurality of methods, said analyzing method comprising:

a first step of measuring any point of the material to be analyzed;

a second step of forming a first model having a plurality of parameters describing the physical properties of the material to be analyzed;

a third step of calculating reference values of the material for the same point, based on measurement results of the first step and the first model;

a fourth step of measuring the same point by a method capable of performing measurement in a shorter time compared to the measurement of the first step;

a fifth step of forming a second model having a smaller number of parameters compared to the first model;

a sixth step of calculating first analytical values of the material for the same point, based on measurement results of the fourth step and the second model;

a seventh step of calculating an approximation formula for approximating the first analytical values to the reference values;

an eighth step of measuring the remaining points by the method of the fourth step;

a ninth step of calculating second analytical values of the material for the remaining points, based on measurement results of the eighth step and the second model;

a tenth step of correcting the second analytical values based on the approximation formula; and a step of displaying the corrected values of the tenth step on a display.

5. An analyzing method for analyzing a material to be analyzed by irradiating light to a plurality of points of the material and measuring a change in the state of reflected light for each point with an analyzing apparatus capable of performing measurement and analysis by a plurality of methods, said analyzing method comprising:

a first step of irradiating light and measuring any point of the material to be analyzed;

a second step of forming a first model having a plurality of parameters describing physical properties of the material to be analyzed;

a third step of calculating reference values of the material for the same point, based on measurement results of the first step and the first model;

a fourth step of irradiating light and measuring the same point by a method capable of performing measurement in a shorter time compared to the measurement of the first step;

a fifth step of forming a second model having a smaller number of parameters compared to the first model;

a sixth step of calculating first analytical values of the material for the same point, based on measurement results of the fourth step and the second model;

a seventh step of calculating an approximation formula for approximating the first analytical values to the reference values;

an eighth step of irradiating light and measuring the remaining points by the method of the fourth step;

a ninth step of calculating second analytical values of the material for the remaining points, based on measurement results of the eighth step and the second model;

a tenth step of correcting the second analytical values based on the approximation formula; and a step of displaying the corrected values of the tenth step on a display.

6. A measuring apparatus for measuring physical properties of a material to be measured, at a plurality of points of the material, comprising:

a first measuring section for measuring any point of the material to be measured;

a second measuring section for measuring a plurality of points by a method capable of performing measurement in a shorter time compared to the first measuring section; and a controller performing operations of:

calculating an approximation formula for approximating results of measuring the same point by the second measuring section to measurement results obtained by the first measuring section;

correcting results of measuring the remaining points by the second measuring section, based on the approximation formula; and displaying the corrected results on a display.

7. An analyzing apparatus for analyzing a material to be analyzed by measuring physical properties of the material at a plurality of points of the material, comprising:

a first measuring section for measuring any point of the material to be analyzed;

a second measuring section for measuring a plurality of points by a method capable of performing measurement in a shorter time compared to the first measuring section; and a controller performing operations of:

forming a first model having a plurality of parameters describing the physical properties of the material to be analyzed;

forming a second model having a smaller number of parameters compared to the first model;

calculating reference values of the material for the same point, based on measurement results obtained by the first measuring section and the first model;

calculating first analytical values of the material for the same point, based on results of measuring the same point by the second measuring section and the second model;

calculating an approximation formula for approximating the first analytical values to the reference values;

calculating second analytical values of the material for the remaining points, based on results of measuring the remaining points by the second measuring section and the second model;

correcting the second analytical values based on the approximation formula; and displaying the corrected values on a display.

8. An ellipsometer for irradiating polarized light to a plurality of points of a material to be measured and measuring a polarization state of reflected light for each point, comprising:

a first measuring section for irradiating light and measuring any point of the material to be measured;

a second measuring section for irradiating light and measuring a plurality of points by a method capable of performing measurement in a shorter time compared to the first measuring section; and a controller performing operations of:

calculating an approximation formula for approximating results of measuring the same point by the second measuring section to measurement results obtained by the first measuring section;

correcting results of measuring the remaining points by the second measuring section, based on the approximation formula; and displaying the corrected results on a display.

9. The ellipsometer according to claim 8, wherein the first measuring section comprises a spectrometer, and the second measuring section comprises a measuring section capable of measuring each wavelength of light simultaneously.

10. An ellipsometer for analyzing a material to be analyzed by irradiating polarized light to a plurality of points of the material and measuring a polarization state of reflected light for each point, comprising:

a first measuring section for irradiating light and measuring any point of the material to be analyzed;

a second measuring section for irradiating light and measuring a plurality of points by a method capable of performing measurement in a shorter time compared to the first measuring section; and a controller performing operations of:

forming a first model having a plurality of parameters describing physical properties of the material to be analyzed;

forming a second model having a smaller number of parameters compared to the first model;

calculating reference values of the material for the same point, based on measurement results obtained by the first measuring section and the first model;

calculating first analytical values of the material for the same point, based on results of measuring the same point by the second measuring section and the second model;

calculating an approximation formula for approximating the first analytical values to the reference values;

calculating second analytical values of the material for the remaining points, based on results of measuring the remaining points by the second measuring section and the second model;

correcting the second analytical values based on the approximation formula and displaying the corrected values on a display.

11. The ellipsometer according to claim 10, wherein the first measuring section comprises a spectrometer, and the second measuring section comprises a measuring section capable of measuring plurality of wavelengths of light simultaneously.

12. A memory product storing a computer program for causing a computer to calculate values concerning measurements at a plurality of points of a material to be measured, said computer program comprising the steps of:

causing the computer to calculate an approximation formula for approximating, to first measurement results of any point of the material to be measured, results concerning the same point of the material to be measured among second measurement results, based on the first measurement results and the second measurement results of the material to be measured, which were measured in a shorter time compared to the first measurement results;

causing the computer to correct results concerning the remaining points among the second measurement results, based on the approximation formula; and causing the computer to display the corrected results on a display.

13. A memory product storing a computer program for causing a computer to analyze a material to be analyzed by causing the computer to receive measurement results at a plurality of points of the material, said computer program comprising the steps of:

causing the computer to form a first model having a plurality of parameters describing physical properties of the material to be analyzed;

causing the computer to form a second model having a smaller number of parameters compared to the first model;

causing the computer to calculate reference values of the material for any point of the material to be analyzed, based on first measurement results of the same point of the material to be analyzed and the first model;

causing the computer to calculate first analytical values of the material for the same point, based on results concerning the same point among second measurement results of the material to be analyzed, which were measured in a shorter time compared to the first measurement results and the second model;

causing the computer to calculate an approximation formula for approximating the first analytical values to the reference values;

causing the computer to calculate second analytical values of the material for the remaining points, based on results concerning the remaining points among the second measurement results and the second model;

causing the computer to correct the second analytical values based on the approximation formula; and causing the computer to display the corrected values on a display.

14. A measuring apparatus for measuring physical properties of a material to be measured, at a plurality of points of the material, comprising:

first measuring means for measuring any point of the material to be measured;

second measuring means for measuring a plurality of points by a method capable of performing measurement in a shorter time compared to the first measuring means;

approximation formula calculating means for calculating an approximation formula for approximating results of measuring the same point by the second measuring means to measurement results obtained by the first measuring means;

correcting means for correcting results of measuring the remaining points by the second measuring means, based on the approximation formula; and means for displaying the corrected results on a display.

15. An analyzing apparatus for analyzing a material to be analyzed by measuring physical properties of the material at a plurality of points of the material, comprising:

first measuring means for measuring any point of the material to be analyzed;

second measuring means for measuring a plurality of points by a method capable of performing measurement in a shorter time compared to the first measuring means;

first model forming means for forming a first model having a plurality of parameters describing the physical properties of the material to be analyzed;

second model forming means for forming a second model having a smaller number of parameters compared to the first model;

reference calculating means for calculating reference values of the material for the same point, based on measurement results obtained by the first measuring means and the first model;

first calculating means for calculating first analytical values of the material for the same point, based on results of measuring the same point by the second measuring means and the second model;

approximation formula calculating means for calculating an approximation formula for approximating the first analytical values to the reference values;

second calculating means for calculating second analytical values of the material for the remaining points, based on results of measuring the remaining points by the second measuring means and the second model;

correcting means for correcting the second analytical values based on the approximation formula; and means for displaying the corrected values on a display.

16. An ellipsometer for irradiating polarized light to a plurality of points of a material to be measured and measuring a polarization state of reflected light for each point; comprising:

first measuring means for irradiating light and measuring any point of the material to be measured;

second measuring means for irradiating light and measuring a plurality of points by a method capable of performing measurement in a shorter time compared to the first measuring means;

approximation formula calculating means for calculating an approximation formula for approximating results of measuring the same point by the second measuring means to measurement results obtained by the first measuring means;

correcting means for correcting results of measuring the remaining points by the second measuring means, based on the approximation formula; and means for displaying the corrected results on a display.

17. The ellipsometer according to claim 16, wherein the first measuring means comprises a spectrometer, and the second measuring means comprises a measuring section capable of measuring plurality of wavelengths of light simultaneously.

18. An ellipsometer for analyzing a material to be analyzed by irradiating polarized light to a plurality of points of the material and measuring a polarization state of reflected light for each point, comprising:

first measuring means for irradiating light and measuring any point of the material to be analyzed;

second measuring means for irradiating light and measuring a plurality of points by a method capable of performing measurement in a shorter time compared to the first measuring means; first model forming means for forming a first model having a plurality of parameters describing physical properties of the material to be analyzed;

second model forming means for forming a second model having a smaller number of parameters compared to the first model;

reference calculating means for calculating reference values of the material for the same point, based on measurement results obtained by the first measuring means and the first model;

first calculating means for calculating first analytical values of the material for the same point, based on results of measuring the same point by the second measuring means and the second model;

approximation formula calculating means for calculating an approximation formula for approximating the first analytical values to the reference values;

second calculating means for calculating second analytical values of the material for the remaining points, based on results of measuring the remaining points by the second measuring means and the second model;

correcting means for correcting the second analytical values based on the approximation formula; and means for displaying the corrected values on a display.

19. The ellipsometer according to claim 18, wherein the first measuring means comprises a spectrometer, and the second measuring means comprises a measuring section capable of measuring plurality of wavelengths of light simultaneously.

* * * * *